US006192168B1

(12) United States Patent
Feldstein et al.

(10) Patent No.: US 6,192,168 B1
(45) Date of Patent: Feb. 20, 2001

(54) REFLECTIVELY COATED OPTICAL WAVEGUIDE AND FLUIDICS CELL INTEGRATION

(75) Inventors: Mark J. Feldstein, Washington, DC (US); Joel P. Golden, Fort Washington; Frances S. Ligler, Potomac, both of MD (US); Chris A. Rowe, Alexandria, VA (US)

(73) Assignee: The United States of America as represented by the Secretary of the Navy, Washington, DC (US)

( * ) Notice: Under 35 U.S.C. 154(b), the term of this patent shall be extended for 0 days.

(21) Appl. No.: 09/288,957

(22) Filed: Apr. 9, 1999

(51) Int. Cl.$^7$ ................................. G02B 6/00; G02B 6/26
(52) U.S. Cl. ............................................. 385/12; 385/30
(58) Field of Search ......................................... 385/12, 30

(56) References Cited

U.S. PATENT DOCUMENTS

| | | |
|---|---|---|
| 5,071,248 * | 12/1991 | Tiefenthaler et al. ............... 356/128 |
| 5,077,210 | 12/1991 | Eigler et al. ............................ 435/176 |
| 5,430,813 | 7/1995 | Anderson et al. ....................... 385/12 |
| 5,512,492 | 4/1996 | Herron et al. .......................... 436/518 |
| 5,677,196 | 10/1997 | Herron et al. .......................... 436/518 |
| 5,736,257 * | 4/1998 | Conrad et al. ..................... 428/474.4 |
| 5,822,472 * | 10/1998 | Danielzik et al. ...................... 385/12 |
| 5,827,748 * | 10/1998 | Golden ................................. 436/527 |
| 6,078,705 * | 6/2000 | Neuschafer et al. .................... 385/12 |
| 6,110,749 * | 8/2000 | Obremski et al. .................... 436/527 |

OTHER PUBLICATIONS

Rowe et al, An array immunosensor for simultaneous detection of clinical analytes, Analytical Chemistry, vol. 71, No. 2, Jan. 15, 1999, 433–439.*

Rowe, et al., An Array Immunosensor for Simultaneous Detection of Clinical Analytes, Analytical Chemistry, vol. 71, No. 2, Jan. 1999, pp. 433–439.

Love et al., "Optical Characteristics of Fiber Optic Evanescent Wave Sensors," SPIE, vol. 990, pp. 175–180 (1988).

Fodor et al., "Light–Directed, Spatially Addressable Parallel Chemical Synthesis," Science, vol. 251, pp. 767–773 (1991).

Anderson et al., "A Fiber Optic Biosensor: Combination Tapered Fibers Designed for Improved Signal Acquisition," Biosensors & Bioelectronics, vol. 8, pp. 249–256 (1993).

Conrad et al., "Photoactivatable Silanes for the Site–Specific Immobilization of Antibodies," Proc. SPIE–Int. Soc. Opt. Eng., vol. 2978, pp. 12–21 (1997).

Brosinger et al., "A Label–Free Affinity Sensor with Compensation of Unspecific Protein Interaction by a Highly Sensitive Integrated Optical Mach–Zehnder Interferometer on Silicon," Sensors and Actuators, B 44, pp. 350–355 (1997).

(List continued on next page.)

Primary Examiner—Frank G. Font
Assistant Examiner—Armando Rodriguez
(74) Attorney, Agent, or Firm—John J. Karasek; Amy L. Ressing

(57) ABSTRACT

A multimode waveguide device for assays includes a multimode waveguide with a patterned, reflective surface coating. The exposed portion or portions of the reflectively coated waveguide surface are for analyte recognition. A fluidics cell is attached to the waveguide so that the channel or channels of the fluidics cell match with the exposed portion or portions of the waveguide surface. The channel or channels direct one or more sample fluids over the exposed portion or portions of the waveguide surface. The reflective coating minimizes loss and scattering of excitation and fluorescence light during a fluorescence assay.

31 Claims, 10 Drawing Sheets

OTHER PUBLICATIONS

Duveneck et al., "Novel Bioaffinity Sensors for Trace Analysis Based on Luminescence Excitation by Planar Waveguieds," *Sensors and Actuators*, B 38–39, pp. 88–95 (1997).

Dübendorfer et al., "Compact Integrated Optical Immunosensor Using Replicated Chirped Grating Coupler Sensor Chips," *Applied Optics*, vol. 37, No. 10, Apr. 1, 1998, pp. 1890–1894.

Wadkins et al., "Detection of Multiple Toxic Agents Using a Planar Array Immunosensor," *Biosensors & Bioelectronics*, vol. 13, No. 3–4, pp. 407–415 (1998).

Mourlas et al., "Novel Interconnection and Channel Technologies for Microfluidics," Conference Proceedings MTAS '98, Oct. 13–16, 1998, pp. 27–30.

Rowe et al., "An Array Immunosensor for Simultaneous Detection of Clinical Analytes," Analytical Chemistry, vol. 71, No. 2, pp. 433–439 (1999).

Ligler et al., "Array Biosensor for Multi–Analyte Sensing," *SPIE*, vol. 3258, pp. 50–55 (1998).

\* cited by examiner

LIGHT COUPLED OUT OF WAVEGUIDE INTO FLOW CELL:
REDUCED EXCITATION INTENSITY ⇒ REDUCED FLUORESCENCE INTENSITIES

SCATTERED LIGHT IN FLOW CELL:
INCREASED SCATTER BACKGROUND ⇒ REDUCED SENSITIVITY

IMAGING ARRAY

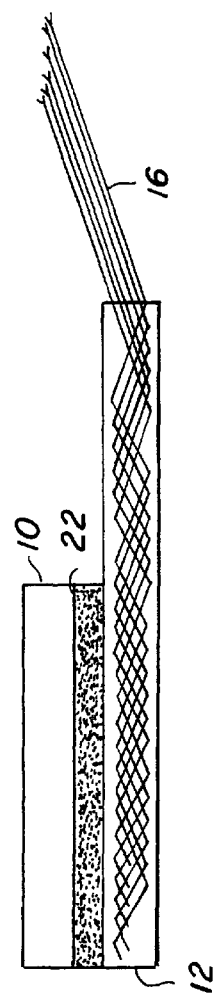
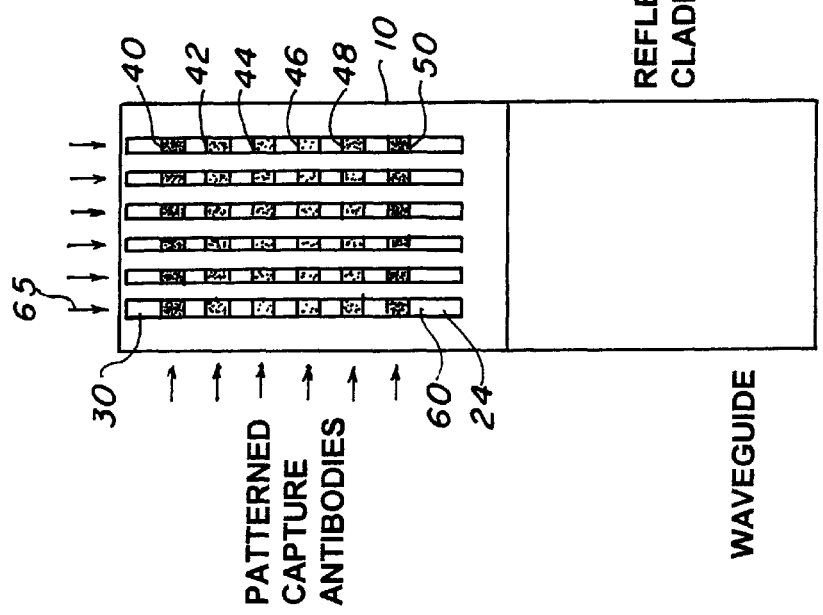
FIG. 3
FIG. 5

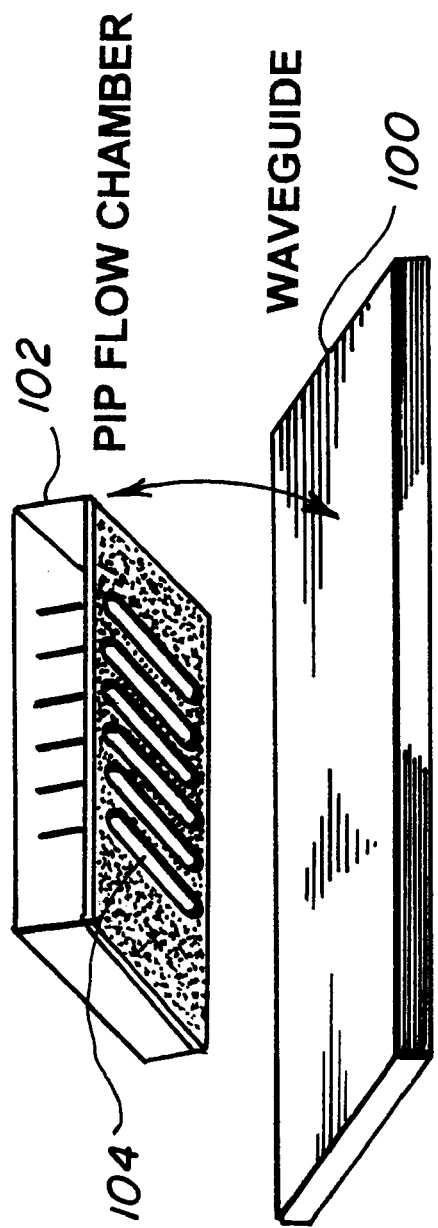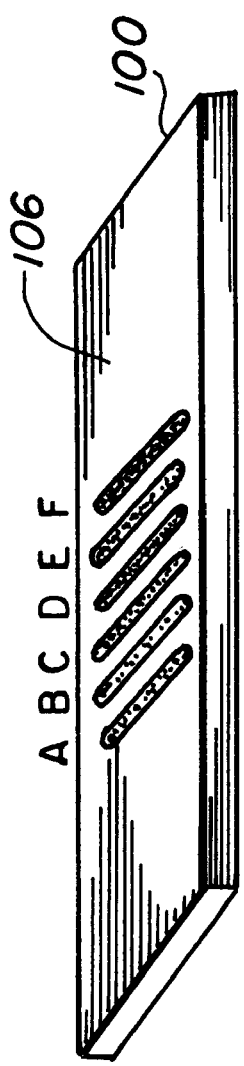
FIG. 7a
FIG. 7b

REFLECTIVELY COATED OPTICAL WAVEGUIDE AND FLUIDICS CELL INTEGRATION

BACKGROUND OF THE INVENTION

1. Field of the Invention

The present invention relates generally to optically transduced assays performed on waveguides and more specifically to assays performed on multimode waveguides.

2. Description of the Background Art

Throughout the present specification, all referenced papers and patents are incorporated herein by reference for all purposes.

In pursuit of the goal of multi-analyte sensing, a variety of methods for immobilizing recognition molecules in arrays and devices for interrogating these arrays have been reported. The array biosensors designed for this goal can be divided into two groups with regard to the method of immobilization and type of molecules immobilized. In the approach pioneered by Fodor and colleagues (Fodor et al., *Science*, 251 767 (1991)), photolithographic activation is used to build up polymers of nucleotides or amino acids in arrays of 1024 elements. These binding molecules are relatively short and only semi-selective: thus, pattern recognition is required for detection. Such systems are becoming widely used for genetic and drug screening where the user wants to screen for a large number of functions or "matches" simultaneously. In the second approach, fully formed molecules such as antibodies or longer nucleic acid strands are attached to the surface (Rowe et al., *Anal. Chem.* 71:(2) 433–439 Jan. 15, 1999; Conrad et al., U.S. Pat. No. 5,736, 257; Conrad et al., *SPIE*, 2978, p. 12 (1997); Wadkins et al., *Biosensors & Bioelectronics*, 13, 407 (1998); Martin et al., *Micro Total Analysis Systems* '98 (Kluwer Academic Publishers, Netherlands, 1998) p. 27). Due to the high specificity of binding, a detection event at a single spot is sufficient for identification. These systems are of more interest to users who want to screen for moderate numbers (i.e., 3–500) of previously identified analytes.

The types of optical devices fabricated for interrogation of these two types of arrays also differ. Instruments for analysis of large numbers of very small elements must have relatively high resolution and are usually based on confocal microscopy. They may often include fairly sophisticated image analysis and pattern recognition software to interpret the semi-selective element responses. Size and weight are not major issues as these devices are intended for use in a laboratory. Instruments for detecting signals from arrays of the second type tend to be geared for portability and low cost (Wadkins et al., supra; Ligler et al., 1998; Herron et al., 1996; Herron et al., 1997; Katerkamp 1997; Duveneck et al., 1995; Düibendorfer and Kunz 1998). The emphasis in this case is on gearing the element size to the device rather than the opposite. The array biosensor described here falls in this latter category and is targeted for use at the bedside for clinical testing, or outdoors for environmental monitoring.

Optical waveguides are advantageous for portable and low cost instruments. In such devices, excitation light traveling in an optical waveguide is confined by total internal reflection (TIR) at the interface defined by the waveguide surface. TIR occurs only under a limited set of conditions and is dependent on a number of factors, including the wavelength, incidence angle, and the relative refractive indices of the waveguide and the surrounding medium (Axelrod et al., *Ann. Rev Biophys. Bioeng*, 13, 247 (1984)). The surrounding medium, referred to as the "cladding", must be of a lower refractive index than the waveguide in order to achieve TIR.

Functionally, designing a system around TIR becomes complex when the goal is not to simply confine light within the waveguide but to use the non-radiative evanescent field generated at the interface to probe material on the waveguide surface. For sensors of this type, it is beneficial to optimize the strength of the evanescent field by maximizing its penetration depth, $d_p$. Given a waveguide and cladding pair of fixed refractive indices, the penetration depth of the evanescent field increases as the optical incidence angle decreases towards the critical angle. The relation is defined by: $d_p ((n_2/n_1)^2 \sin^2 \phi - 1)^{-1/2}$, where $\phi$ is the angle measured from the surface normal and $n_1$ and $n_2$ are the refractive indexes of the surrounding medium and waveguide, respectively, and $n_2 < n_1$ (Love et al., *SPIE*, 990, p. 175 (1988)). However, TIR will not occur beyond a critical angle as derived from Snell's law, where $\sin \phi_{critical} = n_1/n_2$. The critical angle for an air-glass interface is approximately 42° and is 67° for a water-glass interface.

Thus, there is an inherent conflict between maintaining light by TIR and maximizing the evanescent field when a cladding is used on the waveguide. As suggested previously, this conflict becomes problematic when the waveguide will be used not only to confine and transmit light but, also to operate as an evanescent field excitation source or sensor in a low index environment, such as air (n=1) or water (n=1.33). Since appropriate cladding materials with refractive indices in the range between air and water do not readily exist, it is not possible both to maximize the evanescent field in air or water and to confine the light with a cladding by TIR.

This conflict could potentially be resolved by developing the sensor around a tapered waveguide or a mono-mode waveguide designed for an optimum balance between optical confinement and a evanescent field penetration depth (Anderson et al., *Biosensors & Bioelectronics*, 8, p. 249 (1993); Anderson et al., U.S. Pat. No. 5,430,813 (1995); Duveneck et al., *Sensors & Actuators B*, 38–39, 88 (1997)). However, it is preferable for a number of reasons to base the sensor on a multi-mode waveguide. First, multi-mode waveguides can be very simple and inexpensive. For example, the planar waveguides used in the present invention can be commercial quality microscope slides. On the other hand, mono-mode waveguides are typically formed by a precision film deposition method such as vacuum deposition. Such processing, especially given required tolerances on the order of tens of nanometers, yields a relatively expensive waveguide.

A second relative advantage of a multi-mode waveguide is that coupling light into the guide is trivial in comparison with a mono-mode waveguide. All that is required to couple light into the waveguide is to direct the light beam onto the end face at an angle within the waveguide's numerical aperture. Under these conditions, once the light enters the waveguide, it will be confined and guided by TIR. Further, given the relatively large face of a multi-mode waveguide, the positioning of the beam on the end face can vary significantly and still be efficiently coupled into the waveguide. A highly tolerant alignment such as this is ideally suited for a system to be used in the field.

In contrast, with a mono-mode waveguide, which is at most a few microns thick, it is not possible to use simple end-coupling to get light into the guide. Coupling in this manner is further complicated by the inherent multi-mode output of diode lasers since a multi-mode beam cannot be focused as tightly a mono-mode laser beam. Instead, coupling into a mono-mode waveguide is generally achieved using gratings or prisms. However, for a sensor system that is intended to be robust and portable, the very tight angular alignment tolerances inherent in using a grating or prism argue against the use of mono-mode waveguides.

The two-dimensional surface of the waveguide lends itself to spatial patterning of multianalyte array elements and image analysis using only a single wavelength and excitation source and fluorophore. This approach is inherently more flexible and less complicated than trying to resolve multiple wavelengths of different fluorophores within a single element, both in terms of the number of analytes that can be measured simultaneously and by the requirement for complex optics. To this end, a method for forming the spatially patterned sensing elements and the means of measuring signals from a large number of elements has been developed.

Another desirable feature for analytical devices, multisample processing, requires a large number of fluid connections and there are several considerations for connector design (Mourlas et al., *Micro Total Analysis Systems '98* (Kluwer Academic Publishers, Netherlands, 1998) p. 27). First, manipulation of fluids and introduction of samples and reagents to the waveguide should be accomplished with minimal increase in the size of the sensor. In addition, fluid-tight attachments should be accomplished rapidly and simply so that little effort is required by the user to replace sensor elements and analyze additional samples. To this end, a means of attaching mounting brackets to the waveguide-flow cell combination has been developed.

Although the waveguide choice influences many of the patterning and fluidics methods, system development is an iterative process and the choice of fluidics feeds back into the design of the waveguide. Specifically, the problem of attaching a fluidics cell to the waveguide without perturbing the confinement of the excitation light, but still allowing for optimization of the evanescent field in either air or water, must be resolved.

SUMMARY OF THE INVENTION

Accordingly, it is a purpose of this invention to provide a multimode waveguide that can be paired with a fluidics cell (also referred to herein as a flow chamber or a flow cell) in such a way that the fluidic cell causes only zero, negligible, or minimal perturbation of the guided light, resulting in an assay system that allows for optical measurements to be performed on the surface of the waveguide.

It is another object of the present invention to provide a waveguide-based assay system adaptable for simultaneous multianalyte and multisample assays on the surface of the waveguide, the system exhibiting only zero, negligible, or minimal perturbation of the guided light.

It is a further object of the present invention to develop techniques for the manufacture of an efficient waveguide-based assay system having a patterned waveguide surface patterned with biological, chemical, and physically responsive molecules.

These and additional objects of the invention are accomplished by providing a patterned reflective coating on the surface of a multimode waveguide. The patterning results in a waveguide surface having optically exposed regions and reflective regions. The optically exposed regions are analyte-responsive and are capable of direct or indirect interaction with at least one analyte within a subsequently presented sample to provide a detectable signal which correlates with the presence of the analyte in the sample. Typically, this analyte-responsiveness is attained by attaching biomolecular, chemical, or physically sensitive recognition species to the waveguide surface using solutions of low salt concentration.

This waveguide is then paired with a fluidics cell that contains at least one channel for the low of a fluid sample (gas or liquid) over the optically exposed regions. The waveguide and fluidics cell may be designed to provide multisample analysis via multiple discrete sample channels, and, within an optically exposed region, multiple discrete, non-overlapping areas allowing the recognition of multiple analytes in a single sample with that optically exposed region. (If there is no need to distinguish between different analytes within a sample, the detection areas for the analytes may be overlapping.) The two options may also be combined to yield multisample processing and multianalyte detection. In the embodiments shown and described herein, the fluidic cell is attached to the waveguide exclusively or almost exclusively at regions first coated with the reflective cladding (some overlap may occur in these embodiments because of the limitations imposed by stencil-based patterning techniques).

BRIEF DESCRIPTION OF THE DRAWINGS

A more complete appreciation of the invention will be readily obtained by reference to the following Description of the Preferred Embodiments and the accompanying drawings in which like numerals in different figures represent the same structures or elements, wherein:

FIG. 3 is a not to scale, cross-sectional side view of an embodiment of the presently claimed invention, illustrating how the presently claimed invention maintains excitation and fluorescence intensities and minimizes scatter background signals.

FIG. 5 is not to scale cross-sectional top view of a device according to the present invention.

FIG. 7*a* and FIG. 7*b* are not to scale and schematically illustrate how Physically Isolated Patterning (PIP) was used to generate columns of recognition antibodies on the waveguide.

DESCRIPTION OF THE PREFERRED EMBODIMENTS

Figure 1A:
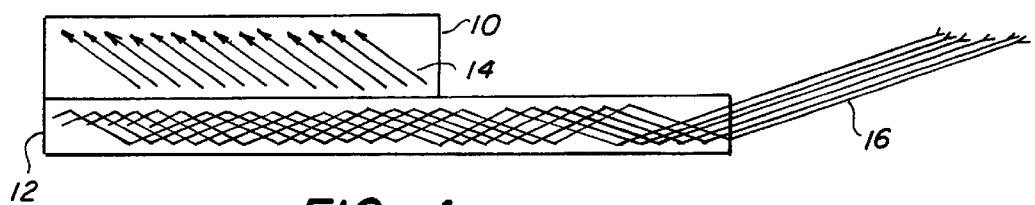
FIG. 1*a* and FIG. 1*b* show the effects of light coupling and scattering, respectively, that would occur when light energy is launched into a waveguide with a fluidics cell attached in a conventional manner (i.e., directly to the waveguide).

The waveguide in the present invention may have any shape, for example cylindrical (e.g., a rod) or planar. Typically, the waveguide used in the present invention is planar. The waveguide may be made of any material that transmits light at both the excitation wavelength and the signal wavelength or wavelengths. Typically, the waveguide is an inorganic glass or a solid such as a polymer (e.g., a plastic such as polystyrene). The waveguide is multimode, which generally allows for lower costs and simpler coupling in comparison to a single mode waveguide.

The reflective coating may be any material that reflects light at the excitation wavelength. Typically, the reflective coating includes a reflective metal, such as aluminum, silver, gold, chromium, platinum, rhodium, or mixtures thereof. More often, the reflective metal is aluminum, silver, or gold. Additionally, the reflective coating can be a multilayer dichroic mirror. The bonding of the reflective coating to the waveguide can be enhanced by providing the reflective coating as a multilayered structure including a reflective layer (which may be the aforesaid reflective metal or dichroic mirror) and a bonding layer between the reflective layer and the waveguide. This bonding layer is selected to enhance adhesion as compared with direct bonding between the waveguide surface and the reflective layer. Preferably, the bonding layer is selected to have minimal or no scattering or absorption of the excitation light. Typical materials for the bonding layer include chromium, platinum, rhodium, a dielectric, a silane (particularly a thiol silane), a cyanoacrylate, a polymer, or a mixture thereof. If desired, the outer surface of the reflective layer (used by itself or as part of multilayer structure with the bonding layer) may be provided with a protective coating to protect the reflective layer from chemical or mechanical damage. Typical materials for the protective coating include chromium, platinum, rhodium, a dielectric, a polymer, or a mixture thereof.

A reflective coating may be applied to the surface of the waveguide in any manner. Typical methods for patterning metal or other reflective coatings on glass or plastic substrates include masked vacuum evaporation of the reflective coating, photolithography, and electroless deposition. The same or similar processes may be used to provide the reflective coating as a multilayer structure.

The optically exposed regions of the patterned waveguide surface are sensitive (i.e., responsive) to at least one of the analytes in question, so that direct or indirect interaction of the optically exposed regions with at least one of the analytes in question alters the optically exposed regions. This alteration may be directly or indirectly detectable by launching an evanescent field generating light wave into the waveguide. For example, the surface of the optically exposed region of the waveguide may be made sensitive to at least one of the analytes in question by being coated with a layer that undergoes an absorbance or luminescence change by reaction with the analyte, or the surface of the optically exposed region may be made sensitive to one of the analytes in question by being coated with biomolecular recognition species.

If the optically exposed region of the waveguide surface is sensitized to the analyte by attachment with or otherwise coating with a biomolecular recognition species, the biomolecular recognition species is typically a protein (e.g., antibody, antibiotic, and an antigen target for an antibody analyte, cell receptor proteins), a nucleic acid (e.g., DNA and RNA), cell, or cell fragment.

Analyte responsiveness in the optically exposed regions may also be accomplished by means other than the attachment of a biomolecular recognition species. For example, the optically exposed area of the surface may be coated with a doped or undoped polymer or sol-gel that exhibits a differential optical response upon exposure to the analyte or the analyte in combination with an additional label or labels. An example of one such non-biomolecular recognition species is provided in MacCraith, B D, *Sensors and Actuators B.,* 29:(1–3) 51–57 October 1995.

Regardless of how analyte responsiveness is achieved, the label is typically a luminescent label (such as a fluorescent label or a phosphorescent label). If a sandwich assay is desired, the labeled secondary molecular species may be any labeled species that recognizes a molecular binding site on the bound analyte or the immobilized biomolecular recognition species/bound analyte complex.

If the surface of the optically exposed region is coated with biomolecular recognition species, either a competitive assay (labeled and unlabeled analyte compete for open binding sites), a displacement assay (unlabeled sample analyte dissociates bound, labeled analyte/biomolecular recognition species) on a waveguide that has been previously saturated with bound, labeled analyte) or a sandwich assay (sample analyte binds to a primary biomolecular recognition species on the waveguide surface, and a labeled secondary molecular species that binds to the immobilized analyte or the immobilized analyte/primary molecular species complex), or any other type of bioaffinity/chemical assay may be employed.

In general, it's best to maintain the reflective coating, and any component layers thereof between the waveguide and the reflective layer of any composite reflective coating, at a minimum thickness need to achieve the intended purpose of the overall coating (reflective coating bonded to the waveguide) and its subcomponents (bonding between waveguide and reflective layer (bonding layer), reflection of excitation light (reflective layer)), to reduce overall bulk and to minimize potential scattering from the non-reflective layers. The thicknesses of the adhesive layer between the reflective coating and the fluidics cell, and the thickness of the protective layer are not optically significant and therefore may be any useful thickness.

Where a waveguide for a bioaffinity assay is desired, if the reflective coating is applied before attachment of the biomolecular recognition species, particular care may be taken to assure that the biomolecular recognition species is immobilized to the optically exposed waveguide regions of the waveguide surface under conditions that maintain the integrity of the reflectively coated portions. Typical methods for attaching biomolecular recognition species to surfaces include covalent binding, physisorption, biotin-avidin binding (such as described in Rowe, supra), or modification of the surface with a thiol-terminated silane/heterobifunctional crosslinker as in Eigler et al. (sic), U.S. Pat. No. 5,077,210 issued Dec. 31, 1991.

As stated above, any protocol for the attachment of molecular recognition sites to the surface of the waveguide must avoid delamination or other destructive modification of the reflective coating. In the biotin-avidin and thiol silane methods, avoiding delamination and destructive modification of the reflective coating typical requires that all solutions to which the reflective coating is exposed during attachment of the biomolecular recognition species have a salt concentration significantly below the physiological salt concentration (the physiological salt concentration is typically about 150 mM). Usually, the salt concentrations used for attachment of biomolecular recognition species to the optically exposed region or regions of the waveguide are less than about one-half of the physiological salt concentration (i.e., less than about 75 mM). More often, the salt concentrations used for attachment of biomolecular recognition species to the optically exposed region or regions of the waveguide are about one-thirtieth to about one-half the physiological salt concentration (i.e., about 5 mM to about 75 mM). Even more often, the salt concentrations used for attachment of biomolecular recognition species to the optically exposed region or regions of the waveguide are about one-thirtieth to about one-eighth the physiological salt concentration (i.e., about 5 mM to about 19 mM). If the salt concentration is too high, delamination results. If the salt concentration is too low, the molecular binding species may lose their functionality. At any given salt concentration, the extent of delamination may be reduced by performing the attachment chemistries at lower temperature (above freezing of course). However, low temperatures during attachment increase the time required for the binding of the biomolecular recognition species to the waveguide surface. These longer binding times, though, expose the reflectively coated surface to the buffer solution for longer durations, and thus may at some point offset the benefit of lower temperature. Typically, most binding of the biomolecular recognition species to the waveguide surface is performed from between ambient temperatures and about 4° C.

The time during which the reflective coating is exposed to the buffer solution for attachment of the molecular species to the waveguide surface should be the minimum required for coverage of the waveguide surface sufficient to provide a useful detection medium. Ultimately, the balance between the time sufficient to provide useful attachment and preventing delamination (i.e., limiting salt exposure) while having a salt concentration sufficiently high to maintain the functionality of the biomolecular recognition species can be empirically determined based upon the guidelines provided above and in the examples below.

In the above-described technology for attachment of the recognition species to the patterned waveguide, recognition species may also, as a side-effect, be attached to reflective coating. However, because the reflective coating will be covered with the fluidics cell and be optically inactive, this attachment is not generally of significant concern. In some instances, such as where a recognition species is particularly expensive, it may be useful to use other molecular patterning technologies such as stamping or inkjet printing to attach the molecular recognition molecules only on the optically exposed regions of the waveguide surface. When using patterning technologies that do not expose a metallic layer to buffer salts, the exposure time and buffer salt concentration need not be modified.

The fluidics cell may be made of any material compatible with the sample fluid. Typically, the fluidics cell is made of a polymer such as polymethylmethacrylate, polycarbonate, or polystyrene. The fluidics cell should be capable of forming a fluid-tight seal with the reflectively coated portion of the waveguide, either with or without the assistance of an adhesive. The fluidics cell may be either rigid or elastic, and may be a single material or a composite or multilayer structure. In the case of a fluidics cell that is adhered to the waveguide by pressure, without the use of an adhesive, it may be advantageous for the surface of the fluidics cell in contact with the reflectively coated portion of the waveguide to be elastic so as to facilitate the formation of a fluid-tight seal. If the fluidics cell is attached to the reflective coating of the waveguide with the assistance of an adhesive, the adhesive should be compatible with the fluidics cell, the reflective coating, and the sample fluid. It may also be useful to select an adhesive provided without solvents incompatible with any recognition species coated upon the optically exposed portions of the waveguide, and which does not require processing (e.g., heat) incompatible with such recognition species.

The present invention allows the attachment to the waveguide of other components (e.g., optical elements (such as light sources, detectors, lenses, filters, etc.), or mechanical elements (such as mounts, pumps, valves, etc), and electronic elements (such as transistors, microcircuits, displays, etc.)) used in optically-transduced assays without significantly optically perturbing the light-guiding characteristics of the waveguide. By attaching such components or one or more mounts for such components (for example, attaching the mounts or other components by the use of an adhesive) to the reflectively clad region or regions of the waveguide surface, the optical characteristics of waveguide will be essentially unperturbed while gaining the additional functionality of the attached component. These additional components may be attached to the waveguide in addition to or instead of a fluidics cell.

Figure 1B:
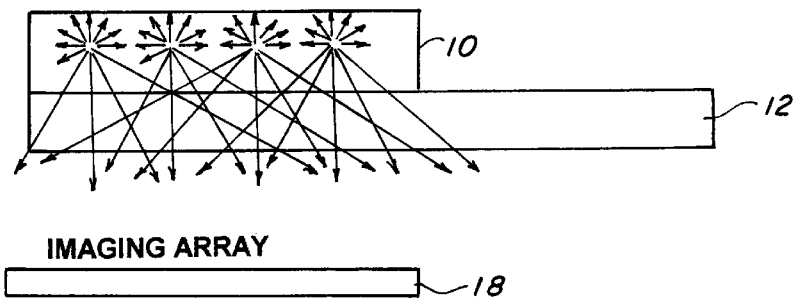

FIG. 1a shows the perturbing effect of the attachment of fluidics cell 10 to conventional waveguide 12 as an out-coupling 14 of excitation light 16 from the waveguide into fluidics cell 10. A further negative consequence of this out-coupling 14, beyond the significant loss of excitation intensity available to perform optical measurements on the waveguide surface, is shown in FIG. 1b. Specifically, and of adverse consequence, the excitation light 16, once it has entered fluidics cell 10, will be scattered in all directions as shown by the arrows in FIG. 1b, including towards the detector element, thus yielding additional optical background and noise at imaging array 18. This additional optical background and noise limits the ultimate sensitivity of any measurements made on the surface of waveguide 12.

Figure 2:
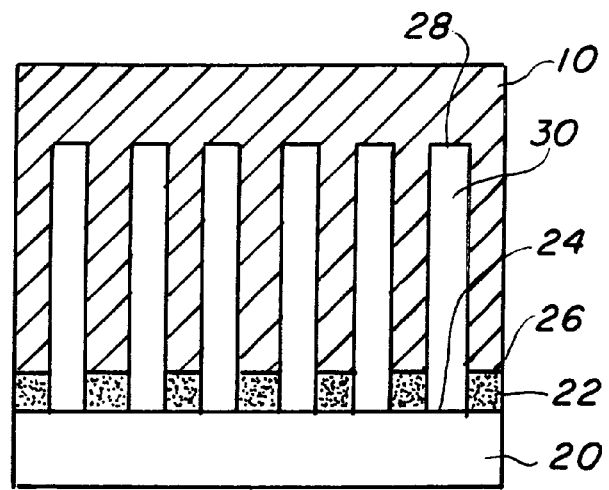
FIG. 2 is a not to scale, cross-sectional view of a reflectively coated multimode waveguide having a fluidics cell attached thereto, according to an embodiment of the presently claimed invention.

FIG. 2, which is not to scale, shows a cross-sectional view of fluidics cell 10 attached to a waveguide having a patterned reflective coating thereon. Waveguide 20 includes a patterned reflective coating 22 on its upper surface that leaves optically exposed regions 24. Bottom surface 26 of fluidics cell 10 has depressions 28 formed therein. These depressions form fluid channels 30 that are bounded in part by optically exposed regions 24 on the upper surface of waveguide 20. Each fluid channel 30 has a sample introduction port 32 (shown in FIG. 5). Because each fluid channel 30 is independent (between fluid channels 30, bottom surface 26 of fluidics cell 10 forms a seal with reflective coating 22 or an adhesive between them) multiple samples may be analyzed simultaneously.

FIG. 3 is a side view (not to scale) of a device according to the presently claimed invention, and illustrates how the presently claimed invention provides improved results for assays using evanescent wave excitation. Excitation light 16 is maintained within waveguide 12 after attachment of the fluidics cell 10 because the reflective coating 22, patterned to match the contact points of fluidics cell 10, eliminates the out-coupling of light into the fluidics cell 10. In this manner, it is possible to attach fluidics cell 10 to the waveguide and perform optical measurements before, during, and after exposure to samples introduced through flow channels in fluidics cell 10.

Figure 4:
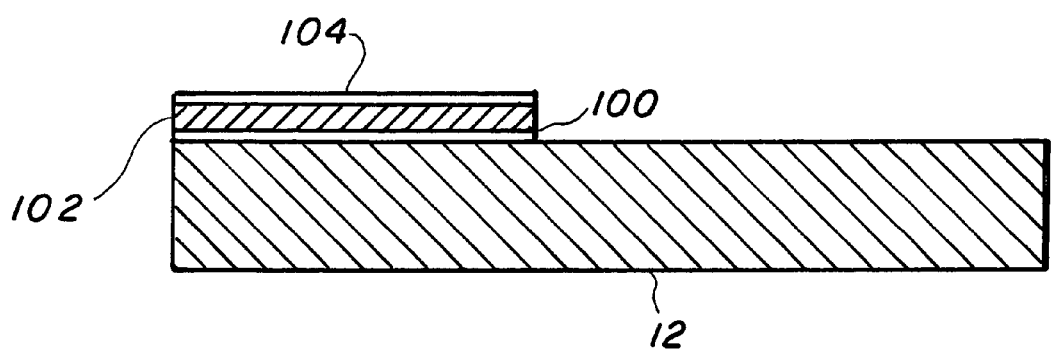
FIG. 4 is a not to scale cross-sectional side view of an embodiment of the present invention in which the reflective coating is a multilayer coating.

FIG. 4 is a not to scale side view of a device according to the present invention showing, in greater detail, a typical embodiment for reflective coating 22 (which may sometimes be referred to herein as a reflective cladding), which appears in FIG. 2. In this embodiment, reflective coating 22 is a multilayered structure including a bonding layer 100, a reflective layer 102, and a protective layer 104.

FIG. 5 (also not to scale) is a top view of a cross-section of the assembled device shown in FIG. 1. Stripes 40 through 50 of molecular recognition molecules extend along the width of the surface of waveguide 12, across both the reflectively coated regions and the optically exposed regions. Strips 40 through 50 may be stripes of biomolecular recognition species for the same analyte, or may be stripes of molecular species for different analytes. Where stripes 40 through 50 are stripes for of molecular species for different antibodies, the presently claim invention allows for simultaneous assaying for different analytes. Attached fluidics cell 10 covers the patterned reflective coating (not visible through fluidics cell 10). Together exposed regions 24 of waveguide 12, fluidics cell 10 forms flow channels 30. Each flow channel 30 may include a separate sample introduction port 65. Thus, in the FIG. 5 embodiment, six different samples may be simultaneously assayed for the presence of six different analytes.

Figure 6:
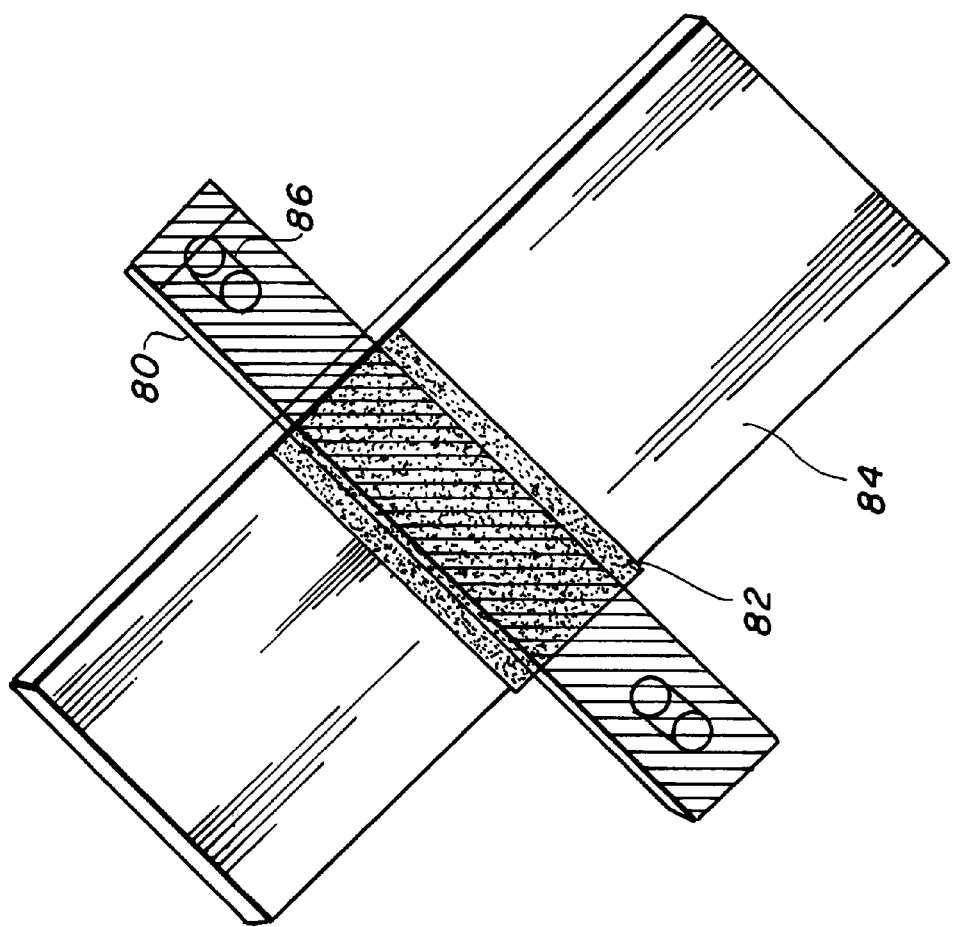
FIG. 6 shows (not to scale) a device according to the present invention in which the reflective coating prevents a device other than a flow cell from perturbing light guided by the waveguide.

FIG. 6 shows an embodiment of the present invention in which the reflective coating prevents perturbation of guided light by attachment of a device 80 other than a fluidics cell. In this embodiment, reflective coating 82 on waveguide 84 is prevent the attachment of device 80 from perturbing guided light in waveguide 84. Device 80 may be a mechanical element mount (such as a mount (with attachment holes 86), pump, a valve, etc), or it may be an optical element (such as a light source, a detector, a lens, a filter, etc.), and/or an electronic element (such as a transistor, a microcircuit, a display, etc.). Device 80 may be present in addition to or instead of a fluidics cell.

Having described the invention, the following examples are given to illustrate specific applications of the invention including the best mode now known to perform the invention. These specific examples are not intended to limit the scope of the invention described in this application.

EXAMPLES

I. Instrumentation and Methods

A. Fluidics

1. Physically Isolated Patterning (PIP)

Figure 8A:
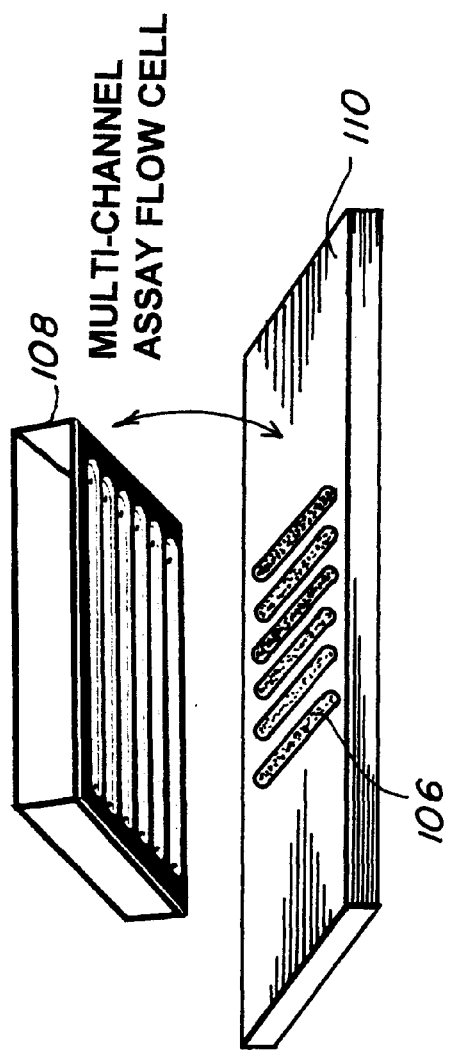
FIG. 8*a* and FIG. 8*b* are not to scale and schematically illustrate the attachment of a multichannel assay fluidics cell to a waveguide having recognition antibodies patterned thereon using the process shown in FIG. 7*a* and FIG. 7*b* to yield combined multisample and multianalyte functionality.
Figure 8B:
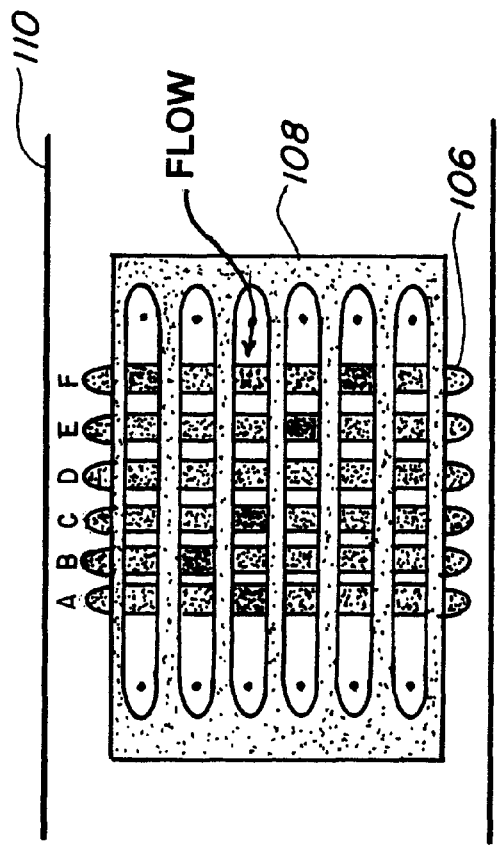

A physically isolated patterning (PIP) method has been developed and used to generate an array of recognition elements, each approximately 1 mm$^2$, on the planar waveguide multi-analyte sensor 100. FIGS. 7a and 7b show the basic steps in PIP process. First, the multi-channel patterning flow cell 102 was placed on the surface of the waveguide 100 which had been functionalized as described previously (Rowe et al., supra). The recognition species, antibodies in this case, were then introduced into appropriate channels 104; each channel 104 contained a separate recognition molecule. After an incubation period, followed by appropriate rinsing, vertically oriented columns 106 of different recognition species were been patterned on waveguide surface 100 (FIG. 7b). When used in combination with a multi-channel assay cell 108 aligned perpendicular to the patterned elements 106 (FIG. 8a) the sensing surfaces were transformed into a 2-dimensional array of rectangular recognition elements (FIG. 8b)

The PIP method, as developed and performed, employed custom designed and molded flow cells consisting of six or more parallel channels, which were fabricated in widths from 0.75 to 1.5 mm (Rowe et al., supra). These cells were made from polydimethylsiloxane (PDMS) (NuSil Silicone Technology), an elastomer known for its ability to mold and reproduce three-dimensional structures. PDMS, once cured, is also highly inert; antibodies and antigens are not degraded during exposure to PDMS (Leslie et al., *Biotechnology and Bioengineering*, (submitted 1998)). In addition, the elasticity and hydrophobicity of PDMS enables temporary, fluid-tight seals to be made utilizing only moderate pressure.

2. Assay Flow Cell

In order to add multi-sample capabilities to the multi-analyte recognition elements, an assay flow cell with six to eight sample channels was attached to the waveguide surface. As shown in FIG. 8b, the assay flow cell 108 was aligned perpendicular to the vertically oriented columns 106 of recognition elements. The result was a two-dimensional array of recognition elements which were grouped to perform independent multi-analyte assays in each assay channel.

Permanent assay flow cells for this device were made from 6.4 mm thick PMMA. The cells, which contain six independent channels for six independent samples, were machined using a CNC milling process. A thin (250 $\mu$m)

pressure sensitive adhesive layer (3M, #9473) was incorporated on the bottom of the cell and employed to make a permanent seal between the patterned glass waveguide and the assay fluid channels. Other adhesives, such as Masterbond EP30 and EP21LV have also been used to seal the flow cells to the waveguide. Inlet and outlet ports were milled into the top of the flow cell to allow each channel to be independently connected to samples and reagents.

Figure 9:
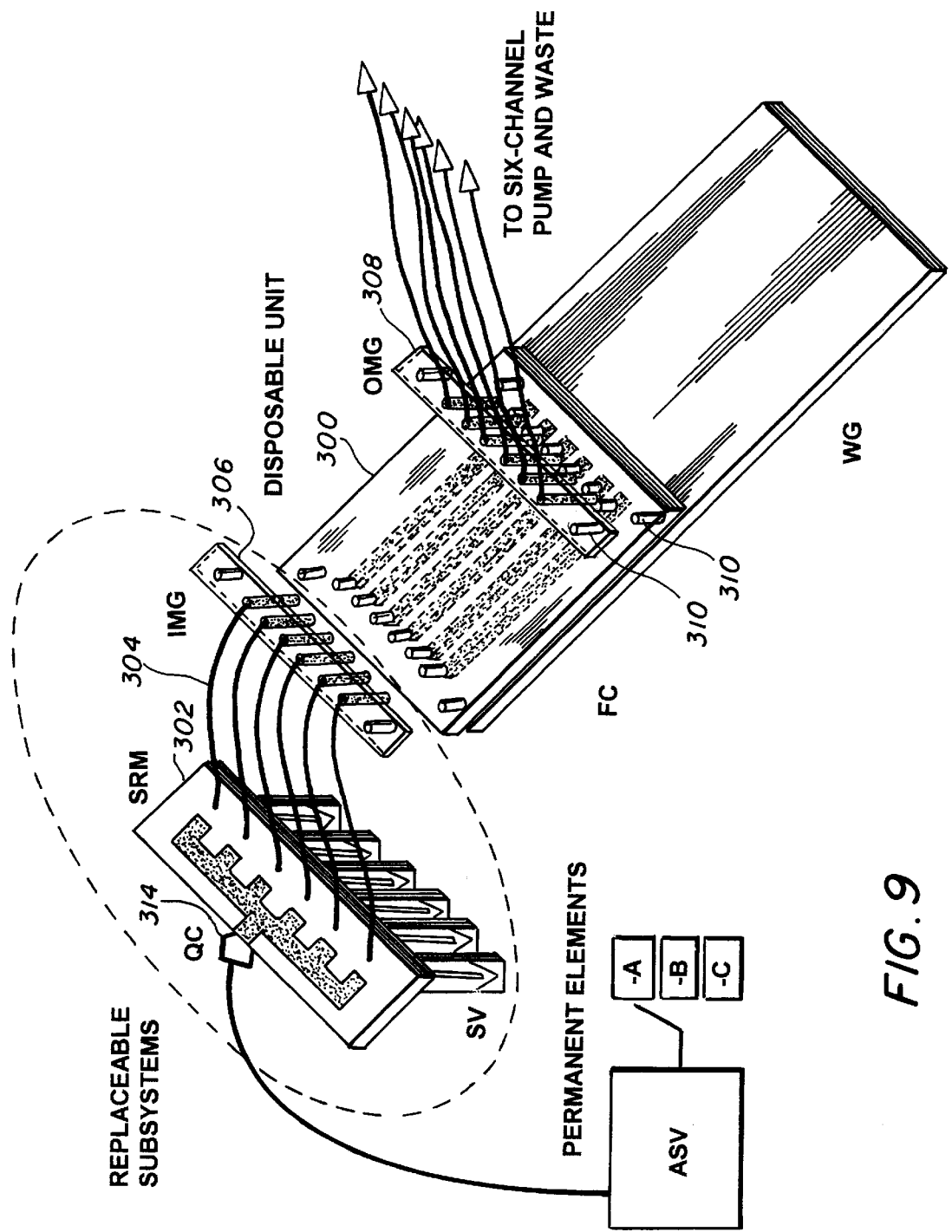
FIG. 9 is not to scale and illustrates a fluidics system consisting of permanent elements, replaceable subsystems, and a disposable unit. The permanent elements included an automated switching valve (ASV) that selected either air (A), buffer (B), or fluorescently labeled antibodies (C), and an output manifold with a gasket layer (OMG) to direct fluids to a six-channel peristaltic pump (not shown). The replaceable subsystem consisted of a sample-reagent manifold (SRM) that drew samples from the sample vials (SV) or reagents, as selected at the switching valve. An input manifold employing a gasket layer (IMG) was used to direct the output of the sample-reagent manifold into the disposable unit consisting of a multi-channel flow cell (FC) permanently attached to a waveguide (WG). Fluidics quick connecter (QC) is used to attach the ASV to the replaceable subsystem.

The valves and pump used in these examples were off-the-shelf commercial components that were computer interfaced to operate the assay protocols in an automated fashion. The system configuration, shown schematically in FIG. 9, utilized a modular multi-position valve (Hamilton, MVP) and an eight-channel peristaltic pump (Ismatic, IPC-8). The system was developed to run directly from the host computer using a high level programming environment (National Instruments, LabWindows) which enabled precise control of all timing issues. This control software can be fully integrated with the image acquisition and data analysis programming. Furthermore, programming modification and adjustments could be made by the user as needed. This flexibility enabled the system to have numerous fluidics procedures ready for use depending upon the desired application. In the current system, fluidic connections between the automated dispensing system and the permanent flow cell 300 were accomplished using a manifold 302 of press-in fittings 304 and a Neoprene gasket to make fluid tight seals to the inlet (306) and outlet (308) ports in the flow cell 300. This format does not significantly increase the sensor size and is a quick, easy connection method. The only steps necessary to replace a six-channel analysis unit are adjustment of four coarse-thread bolts 310, which thread into bolt holes 312 in flow cell 300, and a quarter turn of a fluid quick-connector 314.

B. Waveguide Cladding

1. Waveguide Insulation

The attachment of a flow cell to the waveguide surface significantly reduced the magnitude of the observed signals, yielding a substantial loss in device performance and sensitivity. Two factors, illustrated schematically in FIG. 1a and FIG. 1b were identified to account for this loss in sensitivity, as discussed above.

In order to attach a multi-channel flow cell to the waveguide and minimize the above effects, an alternative to TIR was exploited to confine and guide the excitation light. Specifically, surface reflection was utilized wherein a reflective metallic mirror was applied to select regions on the waveguide surface. This allowed for light to be fully confined within the guide, independent of the angle of incidence at the interface with the attached fluidics components.

The silver-based cladding used to achieve this optical insulation was based on a back-reflector mirror design and consisted of three layers (Opticoat Associates, Protected Silver). First, a transparent dielectric film was applied to the surface of the waveguide to promote adhesion of the second layer, a silver film. Silver, by itself, has very poor adhesion to glass and will easily delaminate. The third and outermost layer was a thin chromium film, which served as a protective layer for the silver reflector.[1]

[1]For a front surface mirror, the ordering of these layers is commonly reversed and chromium is used to promote adhesion. However, a chromium underlayer significantly reduced the optical throughput of the waveguide and was not suitable for this application.

The pattern of the silver cladding covered the area where a six-channel flow cell made contact with the waveguide. The rest of the waveguide surface was left uncoated and was suitable for performing optically transduced immunoassays (FIG. 5). A physical mask was built which, when placed below the planar waveguide surface during the vacuum deposition of the three layer cladding, acted like a stencil by shadowing parts of the surface and allowed only selected areas to be coated by the evaporated materials.

Stability During Immobilization Process

A critical factor was the compatibility of the cladding with the processing conditions necessary to convert the waveguide's optical surface into a sensing element. For example, the surface was derivatized with species including silane, cross-linkers, avidin, and various proteins. Highly reflective silver and aluminum claddings, which were found to be effective optical cladding materials, were unstable in standard biological buffers, such as phosphate buffered saline (PBS) and tris buffered saline (TBS), used to pattern the recognition molecules.

The antibody immobilization protocol (Rowe et al., supra) was changed to yield conditions which still produced an active array of antibodies on the waveguide but which did not cause delamination of the cladding layer.[2] Specifically, low ionic strength buffers were used for all processing steps performed prior to the immunoassay. Additionally, the processing steps were reduced in time by factors of two to fourteen in order to further prevent delamination of the cladding layer.

[2]Antibody immobilization on the waveguides was performed using a modified of standard protocol, as compared to published procedures (Rowe et al. supra; Bhatia et al. supra) in order to be compatible with and not yield delamination of the reflective cladding. Specifically, a thiol silane layer was created on the glass surface by a one hour exposure of the silver-clad waveguide to a 2% percent 3-mercaptopropyl trimethoxysilane in anhydrous toluene. This was in contrast to published protocols calling for longer incubations. An ethanolic solution of the heterobifunctional crosslinker, GMBS, (0.29 mg/ml) was incubated with the silanized waveguide for 30 minutes. Finally, NeutrAvidin was covalently immobilized onto the surface by incubating the GMBS-treated waveguides for one hour with 100 µg/ml NeutrAvidin in 10 mM Na Phosphate, 10 mM NaCl (pH 7.0). The one hour incubation period and lower salt content are in contrast to published protocols calling for overnight incubation in PBS. Biotin-labeled rabbit anti-SEB IgG was patterned on the NeutrAvidin-coated surface using a 20 µg/ml solution in 10 mM sodium phosphate/10 mM NaCl/0.05% Tween 20 in an overnight patterning process. The buffer used for this step and the NeutrAvidin attachment was a modification of published protocols calling for standard PBS-based buffers.

Assays were performed on the antibody patterned waveguides as previously described (Rowe et al., supra). The sensor surface was first rinsed with 1 ml of PBS containing 0.05% Tween 20 and 1 mg/ml BSA (PBSTB). Next, the waveguides were exposed to samples containing flowing SEB at concentration of 100 and 500 ng/ml in PBSTB for 10 minutes. After rinsing slides, waveguides were incubated for 3-minutes with fluorescently labeled anti-SEB (20 µg/ml in PBSTB) followed a final rinse.

C. Optical System

1. Waveguide Excitation

Figure 10:
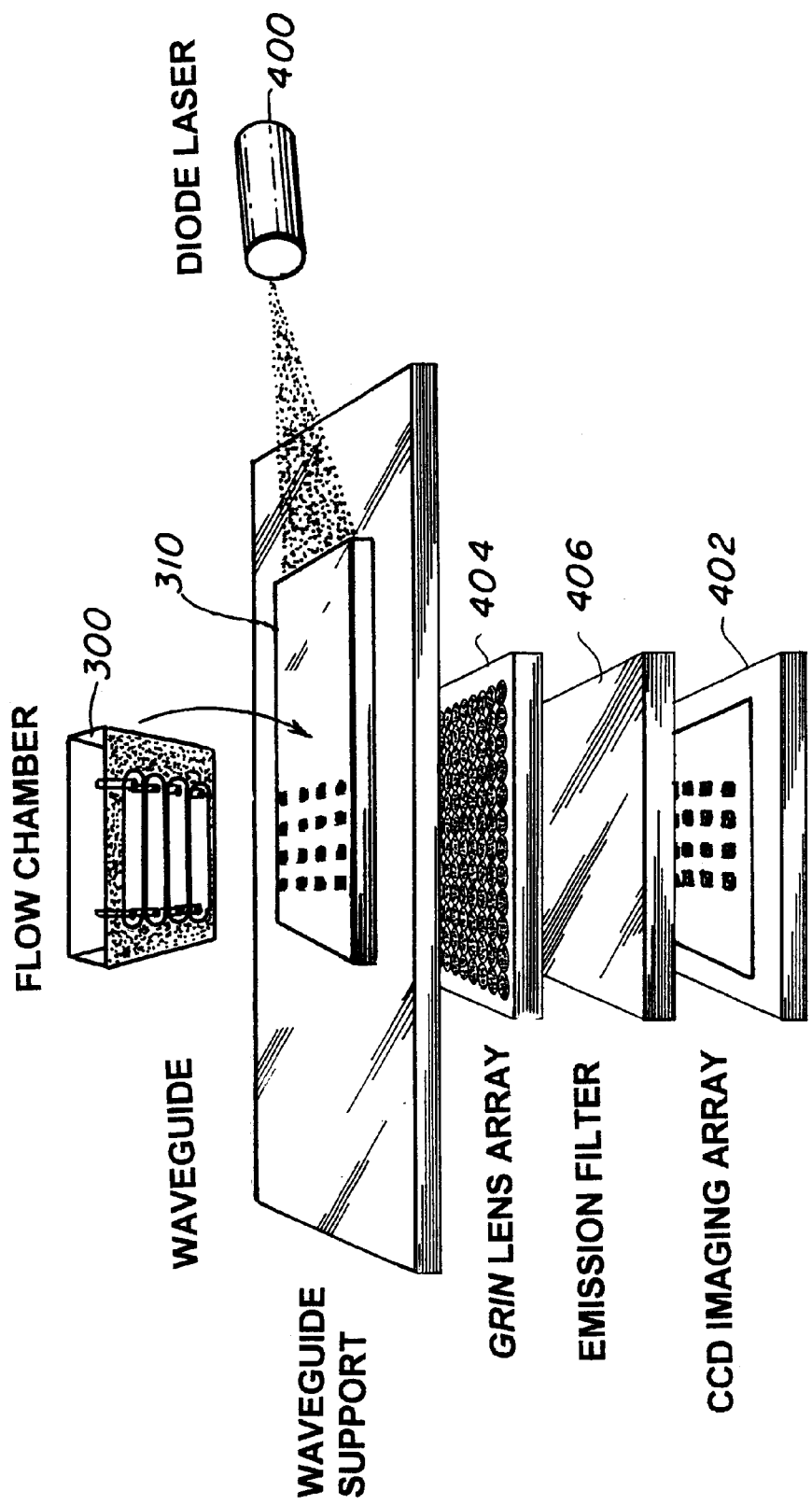
FIG. 10 is not to scale and shows an optical system for use with the presently claimed invention.
Figure 11:
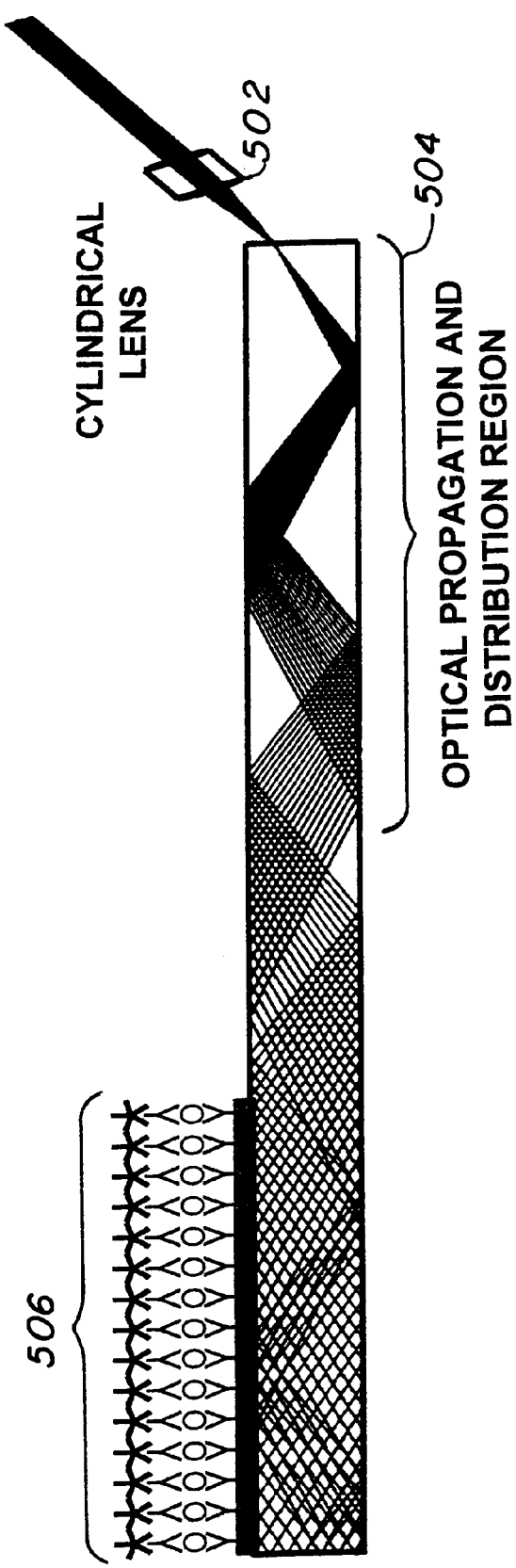
FIG. 11 is not to scale and shows how uniform longitudinal excitation was achieved by using a cylindrical lens to focus the excitation beam into the waveguide and by allowing the beam to propagate and distribute prior to the sensing region.

The waveguide surface was optically interrogated using a diode laser with a output tailored to optimize coupling to and maximize excitation uniformity within the waveguide. As shown in FIG. 10, the beam from a 635 nm diode laser 400 was expanded and launched into the edge of the waveguide 310 (a standard microscope slide), evenly illuminating the entire lateral width of the waveguide 310. A simple line generator (not shown) was used to provide uniform lateral excitation and it successfully yielded lateral uniformity within twenty percent. A cylindrical lens 502 (FIG. 11) in conjunction with a propagation and distribution region 504 in the waveguide provided uniform longitudinal excitation at the sensing region 506. As shown in FIG. 11, this uniformity resulted from the optical beam diverging after it was focused onto the proximal end of the guide and spreading out within the guide prior to the sensing region. The generation of uniformly distributed light within the guide in this manner is a unique application of a cylindrical lens and an internal propagation region as compared to prior methods (Herron, et al. (1997)).

B. Imaging System

To examine the fluorescent pattern from the detection assays, a compact imaging system recorded the spatial orientation of the fluorescent array elements (FIG. 10). Specifically, the evanescently excited fluorescent pattern was imaged onto a large-area, thermoelectrically cooled charge-coupled device (CCD) imaging array 402 (Spectra Source, Teleris). The cooled imager has a lower and more stable electronic background than room temperature imagers. A 670 nm bandpass filter (Corion) and a 665 nm longpass filter (Schott Glass) efficiently rejected scattered excitation light. A non-inverting 2-dimensional graded index (GRIN) lens array (Nippon Sheet Glass) 404 provided 1:1 focusing of the fluorescent image onto the CCD (Golden, U.S. Pat. No. 5,827,748 (1998)).

An optical mounting system facilitated waveguide installation, excitation alignment and image capture. To easily adjust and anchor the focus, the GRIN lens array 404 and emission filters 406 were mounted inside an adjustable alignment scaffolding (not shown). The aluminum top plate of the scaffolding had a 1 mm recess, in the same shape as the waveguide, machined into the surface, and a 1 inch square opening at one end of the recess which allowed for imaging of the fluorescent arrays. The waveguides were easily inserted into and removed from the recess. The diode laser 400 was permanently mounted relative to this scaffolding such that the excitation beam was reproducibly launched into the edge of the waveguide to be imaged. Once the top plate and GRIN lens array 404 scaffold were anchored, there was no need for any optical adjustments before imaging the sensing surface.

II. Results and Discussion

A. Fluidics

1. Assay Flow Cell

A primary benefit of the permanent flow cell, beyond providing the capability of simultaneous multi-sample processing, is that the sensing element becomes a single self-contained unit. Once the flow cell is attached, no user manipulation or alignment is required. In addition, the patterned surface is protected by the flow cell from contamination and damage during storage. Because the flow cells are permanently sealed, the assays can easily be performed while being imaged on the CCD data acquisition system. This system enables accurate, spatially resolved backgrounds to be recorded prior to and during the assay. Finally, in most assays, a single unit can be continuously. In other assays (e.g., sandwich assays) it can be used until a positive sample is detected.

B. Waveguide Cladding

Utilizing the modified immobilization conditions, it was possible to attach antibodies to the waveguide without delaminating silver or aluminum claddings and to perform optical immunoassays without adverse effect on the activity of the biological components. Further, with the cladding and biochemical receptors intact, it was possible to attach a flow cell to the surface of the waveguide with negligible loss of signal from a fluorescence immunoassay.

The silver cladding is not a perfect reflector of visible light and some light in the waveguide is lost due to absorption or scatter. A comparison of the optical throughput of such a waveguide with a similar but unclad waveguide using identical excitation and detection conditions revealed a relative loss of approximately twenty five percent of the excitation intensity after the silver cladding was deposited (data not shown). However, as discussed below, the cladding's utility is clearly demonstrated when a comparison is made between the clad and unclad waveguides with respect to the signal loss for a fluorescence immunoassay due to flow cell attachment. In addition, silver cladding is relatively advantageous over other metallic claddings having an even lower optical throughput. For example, with aluminum cladding, fifty percent of the excitation light was lost. Platinum, which was capable of withstanding the standard immunochemistry processing conditions, transmitted less than twenty-five percent of the excitation light, making it less desirable as an optical cladding material despite its robust adhesion.

Figure 12:
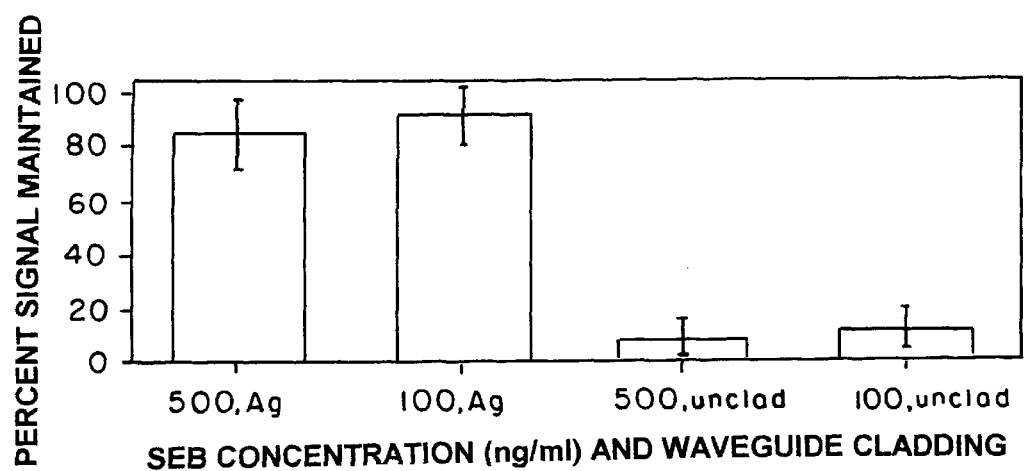
FIG. 12 is a graph showing effect of flow cell attachment measured as the percent of the fluorescent signal that was maintained after the flow cell was attached to the waveguide. Samples containing 100 and 500 ng/ml SEB were analyzed using a standard sandwich immunoassay format on glass waveguides which possessed either silver cladding or which were unclad. Slides were imaged immediately after assay development and again after attachment of the permanent flow cells. Shown are the percent signals maintained after attachment of the flow cells. The initial signals, measured as mean intensity minus the background, were 2262, 1660, 11311, and 5816 units, respectively for the four conditions as shown.

The comparison of the signal loss due to flow cell attachment for assay elements patterned onto the clad and unclad surfaces is striking. Specifically, as shown in FIG. 12, the results from fluorescence sandwich assays using 100 and 500 ng/ml concentrations of *Staphylococcus aureus* Enterotoxin B (SEB), a common food poisoning agent, as the analyte indicate that the glass (unclad) waveguide experiences a substantial loss in signal after the flow cell is attached. In fact, only 10% of the signal is retained. Silver clad waveguides, by comparison, maintain 85–90% of their signal for the same assays after flow cell attachment.

An additional figure of merit, which addresses the net benefit of the reflective cladding, is the ratio of the signal from a waveguide with a flow cell and reflective cladding to the signal from a waveguide with a flow cell but without cladding. Based on the results for 500 and 100 ng/ml SEB assays presented above, the ratio indicates a net gain using cladding of nearly 2.5 times. This gain is critical in that, in part, it directly determines the minimum detection limit above the background; the detection limit being the key attribute of the systems sensitivity. These results using a reflective cladding uniquely enable the integration of an optical waveguide and a flow cell in order to perform optically transduced, biochemical assays on the waveguide surface.

B. Waveguide Excitation Optics

Figure 13:
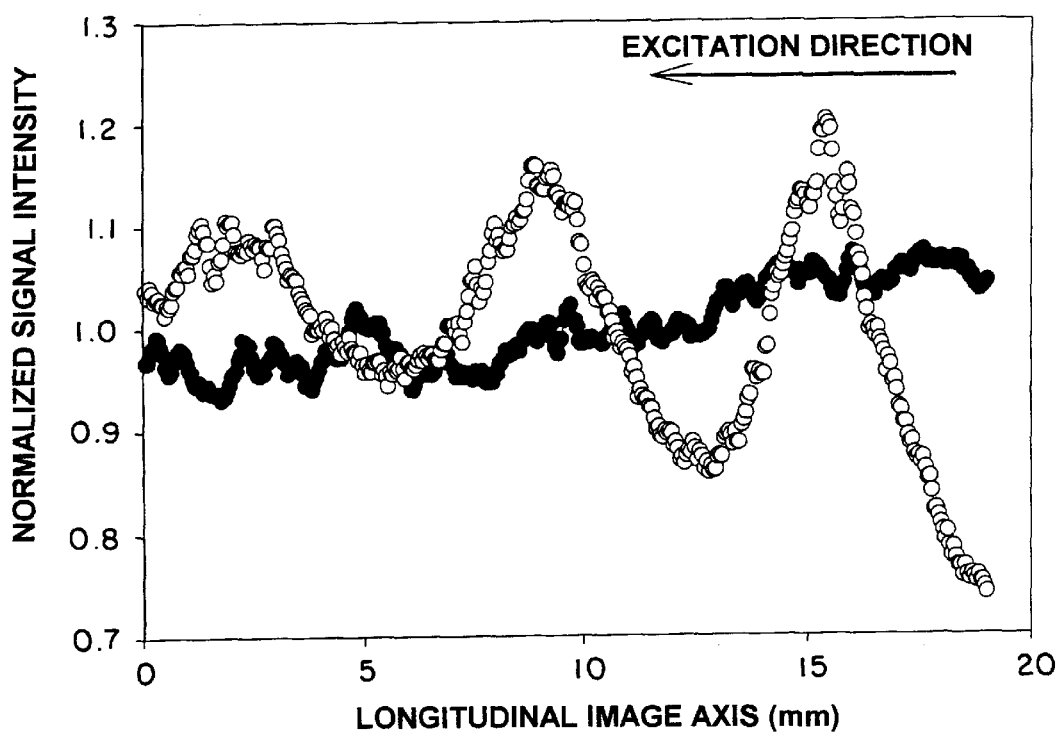
FIG. 13 is a graph showing excitation uniformity. Fluorescent intensities (normalized to their mean value) from a uniformly patterned sandwich immunoassay are shown as a function of their longitudinal position. Direct coupling of a diode laser into the waveguide resulted in substantial modulations of the fluorescent intensities, or "hot spots" (open circles). When a cylindrical lens and propagation region were used, uniform excitation was achieved (filled circles). Each data point represents the mean of 20 pixels measured across the width of the longitudinal line.

Although waveguide excitation is not a primary focus of the presently claimed invention, a brief discussion thereof is provided for context. A system using a cylindrical lens and internal propagation region to homogenize the longitudinal excitation light can be compared with a standard collimated beam coupled into a multi-mode waveguide (FIG. 13). The variation of the signal using the homogenized excitation (• in FIG. 13), as measured by the difference between the minimum and maximum signals, is 14%. This relatively small non-uniformity can be attributed to a natural decay of the excitation intensity due waveguide losses, such as scattering. By comparison, there is a 46% difference between the minimum and maximum signals when the uniformity generating method is not employed (○ in FIG. 13). This large variance is the direct consequence of discrete excitation of localized regions, or "hot spots", as indicated by the periodic modulation of the signal intensity. It is interesting to note that the modulation depth is reduced as the excitation beam propagates (from right to left as shown). This change results from the inherent slight divergence of the diode laser output and the beginning of the excitation beams homogenization as it propagates through the waveguide. Essentially, this line shape depicts the early stage of the uniformity generating process illustrated in FIG. 11.

An additional important benefit of using a cylindrical lens is enhanced coupling and improved alignment tolerance; these factors are important for portable devices. Specifically, the beam is focused down to approximately 250 microns, as compared with a 1000 micron waveguide thickness. Because of the propagation and distribution region, the final measured signal is insensitive to the position of the excitation beam on the proximal end of the waveguide. Thus, alignment variations of up to +/−150% are fully tolerated.

CONCLUSIONS

A patterned reflective cladding on the waveguide uniquely enables direct integration of an attached multi-channel flow cell with a planar waveguide to yield simultaneous multi-analyte, multi-sample processing and optical analysis.

Obviously, many modifications and variations of the present invention are possible in light of the above teachings. It is therefore to be understood that, within the scope of the appended claims, the invention may be practiced otherwise than as specifically described.

What is claimed is:

1. A waveguide device for surface-sensitive optical detection of a first analyte in a first fluid sample, comprising:
   a multimode waveguide having a surface bearing patterned, reflective coating, said patterned reflective coating defining a reflectively coated region and a first optically exposed region on said surface;
   said first optically exposed region being sensitive to said first analyte so as to produce an alteration of said first optically exposed region indicative of the presence of said first analyte in said sample, said alteration being detectable by launching a light wave into said waveguide to generate an evanescent field at said patterned surface, and then detecting an interaction of said first optically exposed region with said evanescent wave.

2. The waveguide device of claim 1, wherein said first optically exposed region includes a first area and a second area, said first area being sensitive to said first analyte so as to produce said alteration of said first area, said second are being sensitive to a second analyte so as to produce said alteration of said second area.

3. The waveguide device of claim 1, wherein said first optically exposed region physically or chemically interacts with said first analyte.

4. The waveguide device of claim 3, wherein said first optically exposed region is coated with an analyte-responsive material, selected from the group consisting of a doped polymer, an undoped polymer, a doped sol-gel, an undoped sol-gel, and mixtures thereof, that exhibits a differential optical response upon exposure to said first analyte or upon exposure to said first analyte and an optically labeled molecule that recognizes said first analyte bound to said material on said first optically exposed region.

5. The waveguide device of claim 1, wherein said first optically exposed region comprises attached biomolecular recognition species.

6. The waveguide device of claim 5, wherein said biomolecular recognition species is a protein, a cell, a cell fragment, or a nucleic acid that recognizes said first analyte.

7. The waveguide device of claim 6, wherein said protein is an antibody.

8. The waveguide device of claim 1, further comprising a light source optically coupled into said waveguide so as to produce an evanescent wave at said first optically exposed region.

9. The waveguide device of claim 8, wherein said reflective coating comprises a reflective layer comprising silver, aluminum, platinum, rhodium, a dielectric, chromium, or a mixture thereof.

10. The waveguide device of claim 9, wherein said reflective layer is a dichroic multilayer reflector including said dielectric.

11. The waveguide device of claim 8, wherein said reflective coating comprises reflective layer and a bonding layer between said reflective layer and said waveguide.

12. The waveguide of claim 11, wherein said bonding layer is chromium, platinum, rhodium, a dielectric, a thiol silane, a cyanoacrylate, a polymer, or a mixture thereof.

13. The waveguide of claim 8, wherein said reflective coating comprises a reflective layer and a protective layer on an outer surface of said reflective layer.

14. The waveguide of claim 13, wherein said protective layer comprises chromium, platinum, rhodium, a dielectric, a polymer, or a mixture thereof.

15. The waveguide device of claim 8, further comprising a detector that detects a first signal generated by said first optically exposed region in response to said evanescent wave.

16. The waveguide device of claim 1, further comprising a mechanical, optical, or electronic component attached to said reflectively coated region of said surface of said waveguide.

17. The waveguide device of claim 1, further comprising:
   a fluidics cell including:
      a first surface having a portion thereof sealed to said coated region, said first surface including a depression therein defining a first fluid channel bounded at least in part by said first optically exposed region;
      a first sample introduction port for the introduction of a sample into said first fluid channel.

18. The waveguide device of claim 17, wherein said patterned surface of said waveguide is planar.

19. The waveguide device of claim 17, wherein said patterned reflective coating includes a second optically exposed region sensitive to said first analyte and first surface includes:
   a second depression therein defining a second fluid channel bounded at least in part by said second optically exposed region of said patterned reflective coating; and
   a second sample introduction port for the introduction of a sample into said second fluid channel.

20. The waveguide device of claim 1, wherein said patterned surface of said waveguide is planar.

21. A method of preparing a waveguide for use in an assay, comprising the steps of:
   providing a multimode waveguide having a surface bearing patterned, reflective coating, said patterned reflective coating defining a reflectively coated region and a first optically exposed region on said surface;
   attaching a first biomolecular recognition species to said first optically exposed region by physically contacting a first area of said first optically exposed region with a deposition liquid including said first biomolecular recognition species and having a salt concentration of no more than about 75 mM for a time sufficient to attach said first biomolecular recognition species to said first area of said first optically exposed region, but for less than an amount of time that results in significant delamination of said reflective coating.

22. The method of claim 21, further comprising the step of attaching a second biomolecular recognition species for a second analyte to a second area of said first optically exposed region by physically contacting said second area of said first optically exposed region with a deposition liquid including said second biomolecular recognition species and having a salt concentration of no more than about 75 mM for a time sufficient to attach said second biomolecular recognition species to said first optically exposed region, but for less than an amount of time that results in significant delamination of said reflective coating.

23. The method of claim 22, further comprising the step of attaching said first and second biomolecular recognition species to a second optically exposed region by:

physically contacting a first area of said second optically exposed region with said deposition liquid including said first molecular species for a time sufficient to attach said first biomolecular recognition species to said first area of said second optically exposed region, but for less than an amount of time that results in significant delamination of said reflective coating; and physically contacting a second area if said second optically exposed region with said deposition liquid including said second molecular species for a time sufficient to attach said second biomolecular recognition species to said second area of said optically exposed region, but for less than an amount of time that results in significant delamination of said reflective coating.

24. A method of performing an assay, comprising the steps of:

providing a multimode waveguide having a surface bearing a patterned, reflective coating, said patterned reflective coating defining a reflectively coated region and a first area of a first optically exposed region on said surface, said first area of said first optically exposed region generating an optical signal, indicative of the presence of said first analyte in said sample, in response to an evanescent wave at said surface;

fixing a fluidics cell to said multimode waveguide, said fluidics cell including:
    a first surface having a portion thereof sealed to said coated region, said first surface including a depression therein defining a fluid channel bounded at least in part by said first optically exposed region; and
    a first sample introduction port for the introduction of a first sample into fluid channel;

introducing said first sample into said fluid channel via said first sample introduction port so that said first sample physically contacts said first optically exposed region;

optically coupling light into said waveguide so as to produce an evanescent wave at said first optically exposed region that has been physically contacted with said first sample;

detecting a first signal generated by said first area of said first optically exposed region in response to said evanescent wave, wherein said first signal is correlated with the presence of said first analyte in said sample.

25. The method of claim 24, wherein said first optically exposed region is coated with a first analyte-responsive material, selected from the group consisting of a doped polymer, an undoped polymer, a doped sol-gel, an undoped sol-gel, and mixtures thereof, that exhibits a differential optical response upon exposure to said first analyte or upon exposure to said first analyte and an optically labeled molecule that recognizes said first analyte bound to said material on said first optically exposed region.

26. The method of claim 25, wherein said first optically exposed region is coated with a second analyte-responsive material, selected from the group consisting of a doped polymer, an undoped polymer, a doped sol-gel, an undoped sol-gel, and mixtures thereof, that exhibits a differential optical response upon exposure to said second analyte or upon exposure to said second analyte and an optically labeled molecule that recognizes said second analyte bound to said material on said first optically exposed region;

and further comprising the step of:
    detecting a second signal generated by said second analyte-responsive material in response to said evanescent wave, wherein said second signal is correlated with the presence of said second analyte in said sample.

27. The method of claim 24, further comprising the step of:

attaching a first biomolecular recognition species for a first analyte to said first area of said first optically exposed region by physically contacting said first area of said first optically exposed region with a deposition liquid including said first biomolecular recognition species and having a salt concentration of no more than about 75 mM for a time sufficient to attach said first biomolecular recognition species to said first area of said first optically exposed region, but for less than an amount of time that results in significant delamination of said reflective coating.

28. The method of claim 27, comprising the step of preparing said multimode waveguide by attaching a second biomolecular recognition species for a second analyte to a second area of said first optically exposed region by physically contacting said second area of said first optically exposed region with a deposition liquid including said second biomolecular recognition species and having a salt concentration of no more than about 75 mM for a time sufficient to attach said second biomolecular recognition species to said second area of said first optically exposed region, but for less than an amount of time that results in significant delamination of said reflective coating;

detecting a second signal generated by said second area of said first optically exposed region in response to said evanescent wave, wherein said second signal is correlated with the presence of said second analyte in said sample.

29. The method of claim 27, wherein said first biomolecular recognition species and said second biomolecular species are different from each other and are selected from the group consisting of proteins, cells, cell fragments, and nucleic acids that recognizes said first analyte or said second analyte.

30. The method of claim 24, wherein said first sample includes an optically labeled analog of said first analyte.

31. The method of claim 24, wherein said introducing step results in any said first analyte in said first sample binding to said first optically exposed region, and further comprising the step of introducing, into said first sample introduction port after said binding of first analyte to said attached first optically exposed region, an optically labeled molecule that recognizes said first analyte bound to said first attached optically exposed region.

* * * * *